United States Patent
Grayzel et al.

(10) Patent No.: US 8,523,887 B2
(45) Date of Patent: Sep. 3, 2013

(54) STIFFENED BALLOON APPARATUS WITH INCREASED FLEXIBILITY

(76) Inventors: Jeffrey Grayzel, Morristown, NJ (US); Joseph Grayzel, Englewood, NJ (US)

( * ) Notice: Subject to any disclaimer, the term of this patent is extended or adjusted under 35 U.S.C. 154(b) by 671 days.

(21) Appl. No.: 12/642,296

(22) Filed: Feb. 11, 2010

(65) Prior Publication Data

US 2011/0077677 A1 Mar. 31, 2011

Related U.S. Application Data

(60) Continuation of application No. 11/226,608, filed on Sep. 13, 2005, now Pat. No. 7,662,163, which is a division of application No. 09/912,008, filed on Jul. 24, 2001, now Pat. No. 6,942,680.

(60) Provisional application No. 60/220,297, filed on Jul. 24, 2000.

(51) Int. Cl.
*A61B 17/32* (2006.01)
*A61M 25/10* (2006.01)

(52) U.S. Cl.
USPC .......... 606/159; 623/1.11; 606/191; 606/194; 606/195; 606/198

(58) Field of Classification Search
USPC ................. 606/159, 108, 191, 194, 195, 198; 623/1.11
See application file for complete search history.

(56) References Cited

U.S. PATENT DOCUMENTS

| 2,701,559 A | 2/1955 | Cooper |
| 3,779,201 A | 12/1973 | Spahn |
| 4,273,128 A | 6/1981 | Lary |
| 4,733,665 A | 3/1988 | Palmaz |
| 4,739,762 A | 4/1988 | Palmaz |
| 4,776,337 A | 10/1988 | Palmaz |
| 4,796,629 A | 1/1989 | Grayzel |
| 5,196,024 A | 3/1993 | Barath |
| 5,209,799 A | 5/1993 | Vigil et al. |
| 5,226,887 A | 7/1993 | Farr et al. |
| 5,242,397 A | 9/1993 | Barath et al. |
| 5,320,634 A * | 6/1994 | Vigil et al. ................. 606/159 |

(Continued)

FOREIGN PATENT DOCUMENTS

| DE | 3402573 | 8/1998 |
| EP | 0623315 A1 | 11/1994 |

(Continued)

OTHER PUBLICATIONS

Yamaguchi, et al. "Update on Cutting Balloon Angioplasty" Journal of Interventional Cardiology, vol. 11, No. 5, Part II. Oct. 1998, pp. S114-S119.

(Continued)

*Primary Examiner* — Vy Q. Bui (57) ABSTRACT

The present invention pertains to a stiffened balloon which can be used in angioplasty, endovascular, and valvuloplasty procedures or as a delivery balloon to deliver a stent or a stent-graft. Longitudinally discontinuous stiffening members connected to the expandable balloon stiffen the balloon but allow it to be navigated through curved passages. Projections on the stiffening members may engage, incise, crush, fracture, or pierce occlusions or retain a stent or stent-graft. Radio-opaque portions may be referenced to determine orientation. Longitudinally continuous stiffening members bearing projections and connected to the balloon perform in a similar manner.

49 Claims, 7 Drawing Sheets

(56) References Cited

U.S. PATENT DOCUMENTS

| | | | |
|---|---|---|---|
| 5,336,178 | A | 8/1994 | Kaplan et al. |
| 5,336,234 | A | 8/1994 | Vigil et al. |
| 5,411,466 | A | 5/1995 | Hess |
| 5,616,149 | A | 4/1997 | Barath |
| 5,647,848 | A | 7/1997 | Jørgensen |
| 5,653,690 | A | 8/1997 | Booth et al. |
| 5,653,696 | A | 8/1997 | Shiber |
| 5,713,863 | A | 2/1998 | Vigil et al. |
| 5,720,726 | A | 2/1998 | Marcadis et al. |
| 5,807,326 | A | 9/1998 | O'Neill et al. |
| 5,810,871 | A | 9/1998 | Tuckey et al. |
| 5,836,965 | A | 11/1998 | Jendersee et al. |
| 5,876,374 | A | 3/1999 | Alba et al. |
| 5,935,135 | A | 8/1999 | Bramfitt et al. |
| 6,007,543 | A | 12/1999 | Ellis et al. |
| 6,013,055 | A | 1/2000 | Bampos et al. |
| 6,027,510 | A | 2/2000 | Alt |
| 6,102,904 | A * | 8/2000 | Vigil et al. .............. 604/500 |
| 6,110,192 | A | 8/2000 | Ravenscroft et al. |
| 6,187,013 | B1 | 2/2001 | Stoltze et al. |
| 6,258,099 | B1 | 7/2001 | Mareiro et al. |
| 6,440,148 | B1 | 8/2002 | Shiber |
| 6,451,049 | B2 | 9/2002 | Vallana et al. |
| 6,569,192 | B1 | 5/2003 | Foreman et al. |

FOREIGN PATENT DOCUMENTS

| | | |
|---|---|---|
| EP | 0808613 | 11/1997 |
| EP | 0834293 | 4/1998 |
| EP | 0974315 | 1/2000 |
| FR | 2753907 | 4/1998 |
| WO | 95/33422 | 12/1995 |
| WO | 96/12517 | 5/1996 |
| WO | 98/07390 | 2/1998 |
| WO | 99/10037 | 3/1999 |

OTHER PUBLICATIONS

A.E. Ajani, et al., Clinical utility of the cutting balloon, J. Invas. Cardiol. 2001; 13:554-557.

M. Adamian, et al., "Cutting balloon angioplasty for the treatment of in-stent restenosis: a matched comparison with rotational atherectomy, additional stent implantation and balloon angioplasty," J. Am. Coll. Cardiol. 2001; 38:672-9.

S. Osula, et al., "Cutting balloon and the three Burrs': treatment for ostial left anterior descending artery in-stent restenosis," J. invas. Cardiol. 2001; 14:93-95.

R.H. Hongo et al., "Cutting balloon angioplasty through stent struts of a 'jailed' sidebranch ostial lesion," J. Invas. Cardiiol. 2002; 14:558-560.

A. Kawamura, et al., "Extraction of previously deployedstent by an entrapped cutting balloon due to the blade fracture," Cathet. And Cardiovasc. Intervent. 2002; 57:239-243.

P. Braun, et al., "Rotablator versus cutting balloon for the treatment of long in-stent restenoses," J. Invas. Cardiol. 2002; 14:291-296.

B.R. Bendok, et al., "Cutting balloon to treat carotid in-stent stenosis: Technical note," j. invas. Cardiol. 2003; 15:227-232.

M.R. tamberella, et al., "Cutting balloon angioplasty to treat carotid in-stent restenosis," J. Invas. Cardiol. 2004; 16:133-135.

G.R. Giugliano, et al., "Cutting balloon entrapment during treatment of in-stent restenosis: An unusual complication an its management," J. Invas. Cardiol. 2005: 17(3); 168-170.

Balan, Octavio, et al., Cutting Balloon Angioplasty for Underexpanded Stent Deployed Through Struts of Previously implanted Stent: J. Invastive Cardiology 14:697-702 (2001).

Raisuke Iijima, et al., The Impact of Cutting Balloon Angioplasty for the Treatment of Diffuse In-Stent restenosis; J. Invasive Cardiology 15:427-431 (2003).

Raqul-Bonan, Cutting or not Cutting: More than 10 Years Later the Cutting Balloon is Around and Still Looking for "The" Indication! J. Invasive Cardiology 15:431:432 (2003).

Remo Albiero, et al., Cutting Balloon Angioplasty for the Treatment of In-stent Restenosis; Cath. & Cardiovasc. Interven. 50:452-459 (2000).

Piero Montorsi, et al., Mechanism of Cutting Balloon Angioplasty for In-Stent Restenosis: An Intravascular Ultrasound Study; Cath. & Cardiovasc. Interven. 56:166-173 (2002).

EPO Supplementary European Search Report, EP 01 96 1714, PCT/US0123284, Grayzel (Nov. 28, 2006).

PCT Notification of Transmittal of International Search Report, Grayzel, PCT/US01/23284 (Jan. 16, 2002).

PCT Written Opinion, PCT/US01/23284, Grayzel (Nov. 22, 2002).

Semba, Charles P., et al., "Abdominal Aortic Aneursym Repair with the W.L. Gore Excluder Endovascular Stent-Graft; Technique and Potential Pitfalls," Techniques in Vascular and Interventional Radiology, 1999, 2(3), pp. 127-132.

Diethrich, Edward B., "AAA Stent Grafts: Current Developments," Journal of Invasive Cardiology, 2001, 13(5), pp. 383-390.

* cited by examiner

STIFFENED BALLOON APPARATUS WITH INCREASED FLEXIBILITY

This application is a continuation of U.S. patent application Ser. No. 11/226,608 filed Sep. 13, 2005, now U.S. Pat. No. 7,662,163, which is a divisional of U.S. patent application Ser. No. 09/912,008, filed Jul. 24, 2001, now U.S. Pat. No. 6,942,680 which claims benefit of U.S. Provisional Application No. 60/220,297, filed Jul. 24, 2000. All of these applications are hereby incorporated herein by reference in their entirety.

FIELD OF THE INVENTION

The invention relates to the field of balloon catheters for angioplasty and the delivery of stents and stent-grafts.

BACKGROUND OF THE INVENTION

Inflatable balloons are employed to dilate stenotic arteries in angioplasty, i.e., percutaneous transluminal coronary angioplasty (PTCA), to dilate stenotic cardiac valves in valvuloplasty, and to deliver and reconfigure stents and stent-grafts. To prevent late lumen loss and restenosis, a stent is carried on a balloon, positioned and expanded to remain in a dilated vessel. Unfortunately, currently available balloon systems for angioplasty and for delivery and expansion of stents often fail to properly deploy the stent to produce a uniform diameter and cross-sectional area along the length of the stent. This results from the very nature of such a cylindrical balloon which is made of a thin, flexible membrane and hence can expand radially to different diameters along its longitudinal dimension. If an obstructive lesion in a blood vessel is of a firmer and less compliant tissue than the normal vascular wall, e.g., fibrous or calcified matter, such tissue presents a much greater resistance than the normal vascular wall to dilatation as the balloon expands. As a balloon is expanded, such stenoses, narrowings, and obstructions impinge upon the expanding balloon to cause an area of relative narrowing or distortion, a so-called "waist". Correspondingly, a stent delivered on such a balloon will suffer from a similar distortion or "waist configuration" as it is conformably expanded with the expanding delivery balloon.

If the stent adopts a "waist configuration", it is generally indicative of inadequate dilatation of the stenotic lesion within the blood vessel. The conventional approach to attempt to remedy this inadequacy has been to increase pressure within the balloon to expand the narrowed area. At times, a separate, higher pressure balloon is utilized. To produce such higher pressure balloons, flexible balloon membranes, which could rupture under increasing internal pressure, were replaced by more rigid balloon materials that permitted much higher internal pressures. However, the more rigid material still has an elastic limit. Balloons made of such material and excessively inflated will be permanently deformed, and may eventually burst. Such deformed balloons are much more difficult to remove from the patient. Moreover, increasing the pressure in the balloon increases the potential for rupture and serious harm to the patient.

Even the use of higher pressures permitted by more rigid balloons are insufficient to dilate some arterial stenoses, particularly if they have an annular configuration. With the stent not completely open and the lumen not fully dilated, the final therapeutic result is less than optimum. Some residual stenoses and a non-uniform cross-sectional area along the length of the stent will result.

Another problem frequently encountered during balloon dilation of stents is the occurrence of flaring of the stent at its ends. Stents are generally manufactured as an independent cylindrical structure or integrated in a sleeve that is slipped onto the balloon and adhered. Conventionally, the balloons are at least slightly longer than the stents that they carry.

As the balloon is inflated and it expands the stent, it typically meets less resistance at the ends of the stent and outside the confines of the stent than it does within the stent. Hence, at full inflation the balloon has a tendency to expand to a slightly larger diameter beyond the ends of the cylindrical stent than at the middle of the stent. The resulting different diameters of expansion are transferred to the stent causing a "trumpet-like" outward flaring of the stent at its ends, which is undesirable.

Additionally, there are several problems with the conventional methodology for delivering a stent to an occlusive site with a conventional balloon catheter. In trying to force the stent inside a tight occlusion, calcified matter or other irregularity at the occlusion often provides resistance against the leading edge of the balloon catheter and may resist entry and positioning of the stent. As the operator tries to advance or withdraw the catheter, the calcified matter or other irregularity may catch hold of the stent and capture it in place while the catheter is moved, causing the stem to separate from the balloon. If the stent is displaced with respect to the balloon, slips partially off the balloon, or separates from the balloon entirely, then the stent will not deploy properly. If the undeployed stent separates from the balloon entirely, retrieving the undeployed stent becomes a very serious problem. Similarly, a stent that is only partially deployed or is incorrectly positioned presents a very significant risk to the patient.

Where an occlusive site is only partially accessible by means of a conventional balloon catheter, i.e., only one end of an occlusion has an inner diameter that is of sufficient size to receive a balloon catheter, expansion of the balloon often causes the entire device to be squeezed and slip out of the occlusive site entirely. Thus, attempts to open such partially accessible occlusive sites often fail. To keep the prior art device within the occlusive site a great deal of force may need to be applied by the operator to prevent the device from slipping out. Such force causes additional stress at the occlusive site and in surrounding structures which present a further risk of rupturing the target site or causing damage to the surrounding areas. This same behavior is also observed in situations where an occlusion is irregular in diameter and the expanded balloon simply slips out of the occlusive site upon reaching a particular state of expansion.

The same difficulties are encountered in attempting to position and deploy a stent-graft with a conventional balloon catheter. Incomplete stent-graft deployment can result in troublesome endoleaks caused by inadequate or otherwise ineffective sealing of the stent-graft at the ends with the interior of the vessel. Such endoleaks allow a channel of blood flow to develop that bypasses the stent-graft, greatly reducing its effectiveness and potentially causing the stent-graft to migrate. Where stent-grafts are deployed to exclude aneurysms, such as in the endovascular repair of an abdominal aortic aneurysm, endoleaks are a very significant problem in that they may allow flow to an aneurysm that could cause the aneurysm to rupture.

U.S. Pat. No. 4,796,629, by one of the present inventors, describes a stiffened dilation balloon which addresses some of these problems by providing an expandable balloon which exerts greater expansion force on localized regions within the lumen. It has been found that the uniform expansion provided by the balloon catheter device described in U.S. Pat. No.

4,796,629 achieves superior results in dilating occluded vessels. As such a stiffened dilation balloon is expanded within an occlusion, the longitudinal stiffener, acting as a rigid beam, transmits expansion force applied to the entire length of the stiffener by the balloon to the localized points of resistance in the vessel. Thus, as compared to a conventional balloon, the force of dilation applied locally is considerably increased and dilatation of highly resistant lesions is greatly facilitated. Such a stiffened dilation balloon is capable of achieving the same degree of dilatation as a standard balloon delivery system but at lower pressures. The stiffeners significantly increase the rigidity of the balloon, reducing variations in the cross-sectional area of the balloon along its length and reducing the occurrence of annular regions with a narrowed waist.

Additionally, it has also been found that an inherent limitation of the balloon catheter device described in U.S. Pat. No. 4,796,629 is its limited maneuverability for deployment in the vascular system. The stiffeners of such a device are fairly rigid, have a fixed length in excess of the turning radius needed to navigate certain pathways and have a fixed, although not necessarily uniform, cross-section. As a result, it can be particularly difficult to navigate the device of U.S. Pat. No. 4,796,629 through the vascular system to reach certain occlusions in smaller vessels without utilizing non-standard entry locations or invasive manual procedures for straightening tortuous vascular pathways.

SUMMARY OF THE INVENTION

The present invention is directed to an improved balloon catheter having an expandable balloon with stiffening members that aid in uniform expansion of the balloon at a target site in a lumen in the human body. The balloon catheter can be used in angioplasty, endovascular, or valvuloplasty procedures, or for the delivery and/or reconfiguration of stents or stent-grafts. The invention is also directed to methods of dilating or expanding a lumen in the body using a balloon catheter. Further, methods for delivering a stent or stent-graft to a lumen in the body using the balloon catheter are provided. In addition, methods for reconfiguring and repositioning improperly deployed stents and stent-grafts are disclosed. It should be understood that use of the term "balloon" in describing the invention encompasses any balloon, chamber or other structure which can be inflated or deflated or otherwise expanded or reduced in size. It should also be understood that use of the term "lumen" in describing the invention encompasses any vessel, fluid path, valve, other flow passage or the like, or the interior volume of any of these.

The balloon catheter of the present invention comprises a catheter having a flow passage for pressurized fluid with an expandable chamber, such as a balloon, connected in-between distal and proximal catheter sections. The expandable chamber is generally bounded by a wall suitably configured for containing a pressurized fluid. A plurality of stiffening members are peripherally disposed along the expandable chamber. Such stiffening members may be embedded in the wall or connected to the inner or outer surface of the wall. The stiffening members generally move with the wall of the expandable chamber and are configured to resist localized deformation in the wall of the expandable chamber.

The stiffening members may be provided with one or more projections that culminate in either a pointed or blunt apex. The projections may function to retain a stent or stent-graft when the chamber is in an unexpanded state, may engage a lumen, and may engage, incise or pierce an occlusion when the chamber is expanded. The stiffening members and the projections may be made radio-opaque so that the balloon or the stent may be precisely located by x-ray imaging.

A stiffening member at the wall of the balloon may be provided with discrete points integral with or connected to the surface of the stiffening member. The points may be configured or positioned to remain enveloped within pleats of the unexpanded balloon or retained below the surface of a stent until the balloon is expanded.

A stiffening member at the wall of the balloon may be provided with stent retention structure integral with or connected to the stiffening member. The stent retention structure may include at least one projection on at least one stiffening member.

The stiffening members may be longitudinally continuous or discontinuous, and may include many individual stiffening elements. The stiffening elements may have a uniform shape, include elements having different shapes, or occur as an array of discrete elements which are adhered or otherwise attached to the expandable chamber. The stiffening members, as well as the individual elements, may act independently or cooperate to form one or more larger structures. Multiple stiffening elements may co-act via one or more attaching elements (e.g., a filament) between individual elements.

Accordingly, it is an object of the invention to further overcome the problems and deficiencies of the prior art.

In particular, it is an object of the invention to provide an improved stiffened balloon for dilatation and stenting, stent retention, vessel engagement and piercing, balloon orientation and balloon maneuverability.

It is an object of the invention to provide a stiffened balloon with greater maneuverability than that of the prior art.

It is another object of the invention to provide improved stiffening members for balloons for angioplasty, valvuloplasty, stent delivery and stent-graft delivery or reconfiguration.

It is another object of the invention to provide improved stiffening members for balloons to engage a lumen and to engage and fracture occlusive material within a lumen.

It is a further object of the invention to provide improved stiffening members for balloons to retain a stent or stent-graft for delivery to or repositioning at a target site in a lumen and for reconfiguring a partially deployed stent or stent-graft.

It is still another object of the invention to provide a stent delivery system for use in angioplasty procedures which achieves full dilation of a stenosis and complete deployment of a stent or stent-graft at the site of an obstructive lesion.

According to an aspect of the invention, a stiffened dilating balloon includes an expandable balloon that includes a plurality of longitudinally discontinuous stiffening members disposed along a perimeter of the balloon; the balloon is made of a flexible material; the stiffening members are less flexible than the balloon; and each stiffening member affects a configuration of an area of the perimeter of the balloon.

According to another aspect of the invention, a stiffened balloon includes an expandable balloon that includes a plurality of longitudinally continuous stiffening members disposed along a perimeter of the balloon; the balloon is made of a flexible material; the stiffening members are less flexible than the balloon; each stiffening member affects a configuration of an area of the perimeter of the balloon; and at least one of the stiffening members includes a projection adapted to temporarily retain a device at the balloon.

According to another aspect of the invention, a stiffened balloon includes an expandable balloon including a plurality of longitudinally continuous stiffening members disposed along a perimeter of the balloon; the balloon is made of a flexible material; the stiffening members are less flexible than the balloon; each stiffening member affects a configuration of an area of the perimeter of the balloon; and at least one of the stiffening members includes a raised surface.

According to a further aspect of the invention, a method of using a stiffened balloon to dilate a lumen and deploy an expandable device includes the steps of: introducing into a lumen a stiffened balloon bearing an expandable device; expanding the balloon and the device to cause at least one projection on a stiffener of the balloon to protrude above an outer surface of the stent and engage an inner surface of the lumen; dilating the lumen; and deploying the device in the lumen.

According to a still further aspect of the invention, a method of using a stiffened balloon to dilate a lumen and deploy an expandable device includes the steps of: interdigitating at least one projection on a stiffener of a stiffened balloon with an expandable device; introducing into a lumen the stiffened balloon bearing the device; expanding the balloon and the device; dilating the lumen; and deploying the device in the lumen.

According to another aspect of the invention, a stiffened balloon includes an expandable balloon including a plurality of longitudinally continuous stiffening members disposed along a perimeter of the balloon; the balloon is made of a flexible material; the stiffening members are less flexible than the balloon; each stiffening member affects a configuration of an area of the perimeter of the balloon; and at least one of the stiffening members includes a pivot point where the stiffening member may be bent to facilitate navigation of the balloon through a passage.

According to a further aspect of the invention, a method of reconfiguring a portion of an expandable device deployed at a lumen includes the steps of: introducing into the lumen a stiffened balloon bearing a longitudinal stiffener at a first location on the balloon; aligning the longitudinal stiffener with the portion of the expandable device; and expanding the balloon to cause the stiffener to exert a first radial force against the portion of the expandable device to reconfigure that portion; and the first radial force is greater than a radial force applied by said balloon at any other location on the balloon.

DETAILED DESCRIPTION OF THE INVENTION

Figure 1:
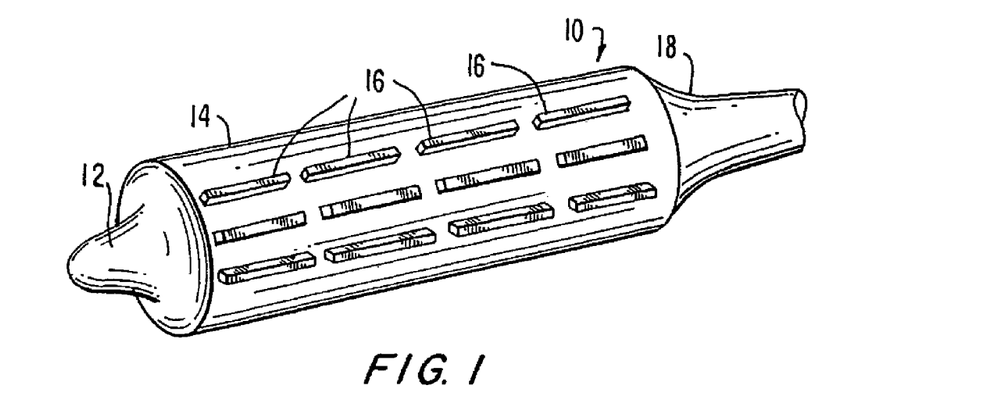
FIG. 1 is a diagram of a closed-ended balloon with discontinuous stiffening members.

FIG. 1 is a drawing of an embodiment of the present invention, indicated generally as device 10, particularly suited for navigating curved or otherwise angled passages. In angiovalvuloplasty procedures, device 10 may be advantageously utilized to access vessels via passages that have curved sections and, in certain embodiments, even passages that include acute angles. Device 10 comprises a balloon having a distal end 12, a balloon 14, discontinuous stiffening members 16 and proximal end 18. Device 10 is generally comprised of standard inert balloon catheter materials suitable for introduction into the human body.

Distal end 12, balloon 14 and proximal end 18 are preferably comprised of a thin, flexible, and generally inelastic material that expands outwardly to assume a predetermined shape at a particular interior pressure, e.g., an envelope with a fixed configuration. Alternatively, end 12, balloon 14 and end 18 are formed from an elastic material. While end 12, balloon 14 and end 18 may be discrete components attached together and have different expansion characteristics, it is preferable that a single contiguous piece of material be used to construct all three.

Distal end 12 defines a volume contiguous with that volume defined by balloon 14. Distal end 12 is shown tapered and closed so that it may be used as a probe for threading device 10 through a lumen. Alternatively, distal end 12 may be arcuate and may have a channel formed in it for the placement of a guide wire on which device 10 could travel. As a further alternative, distal end 12 may be open-ended, e.g., as shown at 42 in FIG. 2.

Balloon 14 comprises a generally cylindrical balloon (as previously defined) which defines a generally cylindrical volume, has a relatively uniform and continuous surface. Preferably, balloon 14 and distal end 12 are formed without seams therebetween and do not leak. Alternatively, balloon 14 may comprise a chamber independent from distal end 12, e.g., without fluidic connection.

Proximal end 18 defines a volume contiguous with that volume defined by balloon 14 and is shown tapered. Preferably, proximal end 18 is open to provide a flow path for fluid to be flowed into balloon 14. Balloon 14 includes a plurality of discontinuous stiffening members 16, preferably aligned along balloon 14 in separate longitudinal rows of stiffening members arranged radially around the perimeter of balloon 14.

The individual stiffening members 16 are preferably made of a uniform material but may be made of different materials. Preferably, individual stiffening members 16 are formed from a flexible metal, plastic or fiber material; a composite material; or the like. Such materials are preferably inert and compatible with usage in the human body. Stiffening members 16 may be smooth or roughened. In an alternative embodiment, stiffening members 16 may be made of the same materials of which the balloon is made. Alternatively, a compatible material that is more rigid than the material of balloon 14 may be used. As a further alternative, a material or composite that is flexible in one direction but rigid in another may be utilized.

The rigidity and flexibility of stiffening members 16 is preferably matched for a desired purpose utilizing the various embodiments of stiffener configurations described herein. Longer and more rigid stiffeners may be advantageously utilized to dilate tougher occlusive material. Shorter and more flexible stiffeners may be advantageously utilized to more easily navigate through contorted passages. Stiffening members 16 may be more rigid than a stent or stent-graft that they carry.

Stiffening members 16 may be attached to balloon 14 by conventional adhesive, constructed as part of the material of balloon 14, patterned as layers upon balloon 14 or embedded in balloon 14. Alternatively, stiffening members 16 may be constructed as part of a sleeve or sheath that is fit over balloon 14 or as part of a sheet that is wrapped around balloon 14.

Device 10 may be attached to a separate catheter apparatus (not shown) or integrated therewith. For example, to attach device 10 to such a catheter directly, proximal end 18 or distal end 12 may be tapered to form a cylindrical section approximately the cross-sectional size of the catheter and bonded to the catheter with a bonding agent or an adhesive, or by ultrasonic welding or the like. Alternatively, device 10 may be folded within a catheter and carried therein.

In operation, device 10 is navigated through passages to a target lumen. The discontinuities in stiffening members 16 and the flexibility of balloon 14 allow device 10 to pass through curved passages by bending device 10 at the discontinuities. Upon reaching the target lumen, a fluid is flowed through proximal end 18 into balloon 14 and distal end 12 to expand balloon 14. Balloon 14 expands radially and stiffening members 16 contact the inner surface of the target lumen. Stiffening members 16 act to focus the expansion force of balloon 14 at the occlusions in the lumen contacted by members 16. As the interior pressure of balloon 14 is increased, members 16 engage, cut, pierce or crush the occlusions, facilitating dilatation of the target lumen by the expanding balloon 14.

Figure 2:
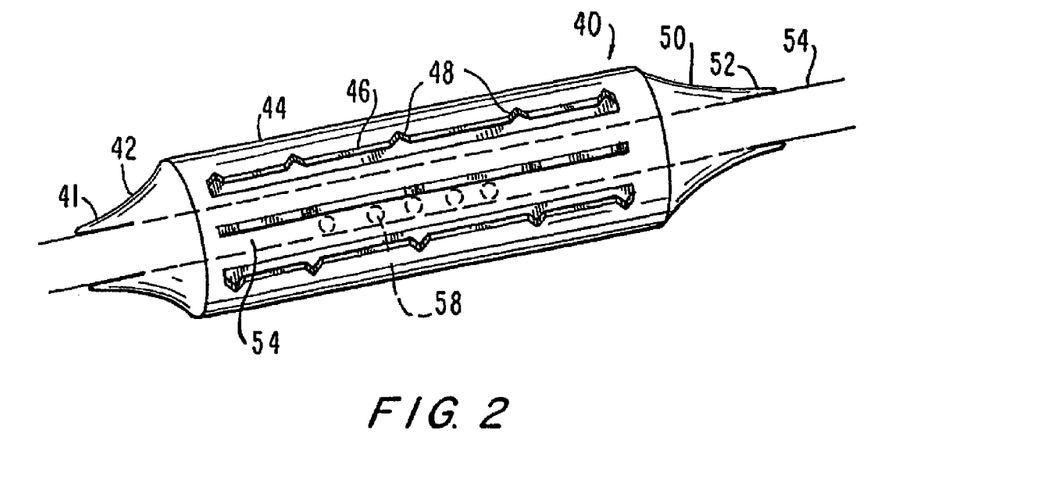
FIG. 2 is a diagram of an open-ended balloon with continuous longitudinal stiffening members having projections.

Another embodiment of the invention, specifically adapted for engaging or piercing occlusions in a lumen is shown in FIG. 2. In FIG. 2, a device 40 comprises a distal end 42, a balloon 44, longitudinal stiffening members 46, and a proximal end 50. A catheter 54 is also shown.

Distal end 42 is the same as distal end 12 except that distal end 42 is open ended. Distal end 42 is shown attached to catheter 54 at seal 41. Seal 41 may be formed with a bonding agent, an adhesive, as a compression seal, or by welding, or the like. As shown, seal 41 is preferably formed by folding the material of distal end 42 inward on catheter 54. Alternatively, seal 41 may be formed by any suitable prior art process for forming a seal between a balloon and a catheter. Preferably, seal 41 provides a fluid-tight seal.

Proximal end 50 is the same as proximal end 18 except that proximal end 50 includes seal 52. Seal 52 may be created by the same processes used to create seal 41. Seal 52 provides a seal between proximal end 50 and catheter 54 and is preferably a fluid-tight seal.

Catheter 54 is a catheter for carrying and inflating balloon 44. As shown, balloon 44 is sealed at seal 41 and seal 52 to catheter 54. Catheter 54 extends through the body of distal end 42, balloon 44, and proximal end 50 as generally indicated at 56. Catheter 54 includes flow holes 58 which provide a flow path for a pressurized liquid to flow from catheter 54 through to the interior volume of balloon 44. Such flow causes balloon 44 to expand. Catheter 54 may carry a flexible guidewire (not shown) that extends through catheter 54 and is slidably adjustable therethrough. Catheter 54 may include a dedicated longitudinal channel specifically for carrying the guidewire.

Balloon 44 is the same as balloon 14 except that balloon 44 bears longitudinally continuous stiffening members 46. One or more of stiffening members 46 includes one or more projections 48. Projections 48 may be attached to or integral with members 46. A plurality of members 46 may be provided on, attached to, or embedded in balloon 44. Stiffening members 46 and projections 48 may be made of the same materials as members 16 and each may be of a different material. Projections 48 may be smooth or roughened. Preferably, projections 48 are 0.004 to 0.015 inches tall and may be shorter or taller, depending upon the application.

As balloon 44 is expanded, members 46 focus radial expansion forces at projections 48 and along the length of each respective member 46. Projections 48 contact occlusions within a lumen to engage, incise, pierce, fracture, or crush the occlusions or to engage an inner surface of the lumen. By engaging the inner surface of the lumen, projections 48 prevent balloon 44 from slipping through a lumen as balloon 44 is expanded.

In an alternate embodiment, balloon 44 is constructed as a closed-ended balloon, e.g., like balloon 14.

Figure 3:
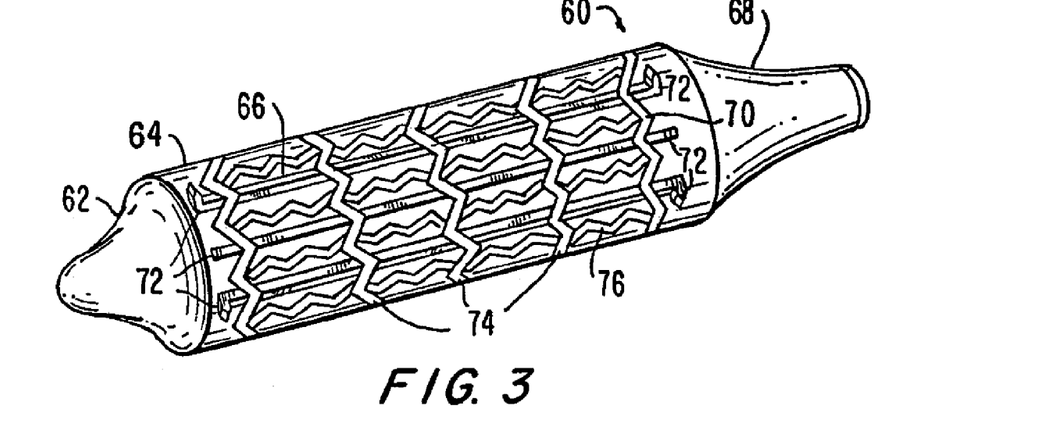
FIG. 3 is a diagram of a closed-ended balloon with continuous longitudinal stiffening members having projections and a stent positioned on the balloon.

In a further embodiment of the invention, FIG. 3 shows a device 60 for deploying a stent 70. Device 60 comprises a distal end 62, a balloon 64, and a proximal end 68. Distal end 62, balloon 64 and proximal end 68 are the same as distal end 12, balloon 14 and proximal end 18, respectively, except that balloon 64 bears stiffening members 66. One or more of stiffening members 66 includes one or more projections 72. Projections 72 are specifically adapted for retaining stent 70 as it is being positioned or guiding stent 70 as it is expanded in a lumen or both. Members 66 and projections 72 may be made of the same material as members 16 and each may be of a different material. Members 66 and projections 72 may be smooth or roughened.

Stent 70 is a conventional stent as known in the art. As shown, stent 70 may include circumferentially expandable members 74 and longitudinally expandable members 76.

In a preferred operation, balloon 64 is expanded and the radial force of expansion is focused by members 66 on portions of stent 70, preferably members 74. Members 66, disposed at intervals along the perimeter of balloon 64 facilitate uniform expansion and deployment of stent 70. Members 66 may match the stent in length or extend beyond the ends of the stent to minimize flaring of the ends of the stent. Projections 72 act to prevent stent 70 from separating from (e.g., slipping off), balloon 64 as balloon 64 is expanded. Alternatively, if members 66 are specifically placed at only selected locations on balloon 64, a custom, non-uniform expansion and deployment of stent 70 can be achieved.

Besides assisting in the expansion of stent 70, device 60 may additionally or alternatively assist in the positioning of stent 70 during a deployment. Projections 72 may hold stent 70 in place on balloon 64 as the entire device is navigated through a passage and precisely located.

As a further alternative, either or both projections 72 and members 66 may be utilized to additionally engage, incise, pierce, fracture or crush occlusions encountered in a lumen during or after deployment of stent 70. Specifically, portions of projections 72 or members 66 may extend radially beyond the surface of stent 70 and may extend through stent 70. Optionally, either or both projections 72 and members 66 may interdigitate with complementary interface structure of stent 70. As illustrated, projections 72 may interdigitate with one or more of expandable members 74 and 76.

The height of projections 72 preferably match the thickness of the device which is carried on the balloon. It is further preferred, where engagement with the lumen is desired, that the height of projections 72 exceeds the thickness of the device carried on the balloon and that such height be even greater where piercing of an occlusion is desired.

In an alternate preferred embodiment, each of projections 72 is configured as a post (see FIG. 10E) which fits within a complementary slot located in stent 70. In general, each of projections 72 may be individually designed to interlock or otherwise removably couple with complementary corresponding structure provided on an expandable device, such as stent 70.

Figure 4:
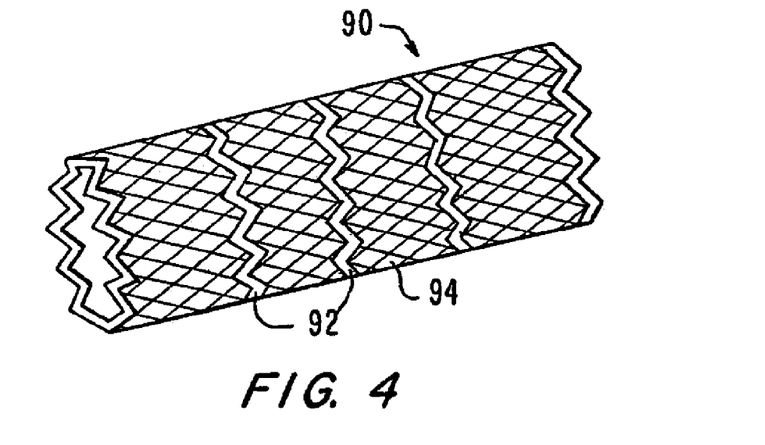
FIG. 4 is a diagram of a stent-graft.

FIG. 4 shows a conventional stent-graft 90 as known in the art. As shown, stent-graft 90 includes expandable radial members 92 and mesh 94. Stent-graft 90 may be substituted with any conventional stent-graft. In the same manner that device 60 may be utilized to position, expand and deploy stent 70, stent-graft 90 may be similarly positioned, expanded and deployed.

Figure 5A:
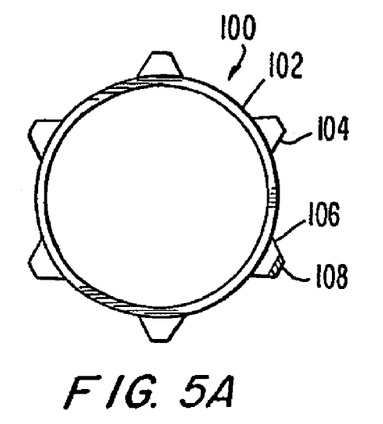
FIGS. 5A, 5B, 5C and 5D are diagrams showing cross-sectional views of balloons with projections.
Figure 5B:
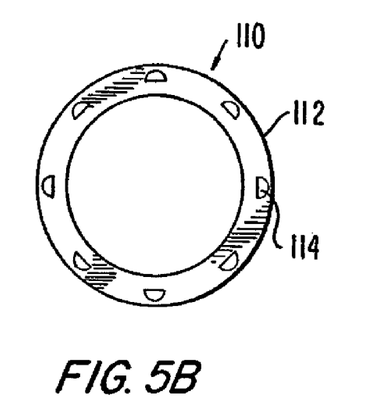
Figure 5C:
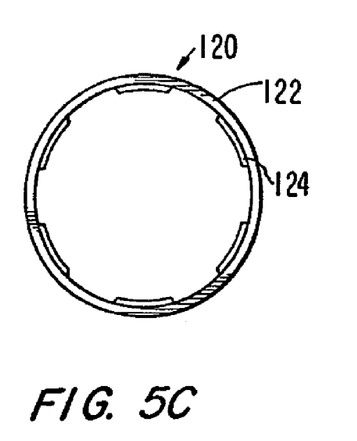
Figure 5D:
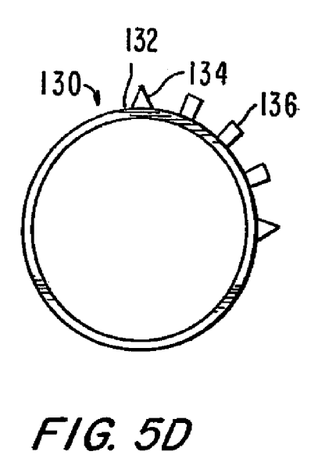

In each of devices 10, 40 and 60 the respective stiffening members may be positioned on the outside of the balloon as shown in FIG. 5A, in the balloon material as shown in FIG. 5B, on the inside of the balloon as shown in FIG. 5C, or collected in a selected area as shown in FIG. 5D.

FIG. 5A shows a cross-sectional view of a device 100 comprising a balloon 102 according to the present invention having evenly-spaced external stiffening members 104. Also shown is a stiffening member 106 having a radio-opaque portion 108. Portion 108 may be made radio-opaque as described hereinbelow. FIG. 5B shows a cross-sectional view of a device 110 comprising a balloon 112 according to the present invention having embedded stiffening members 114. FIG. 5C shows a cross-sectional view of a device 120 comprising a balloon 122 according to the present invention having internally-located stiffening members 124. FIG. 5D shows a cross-sectional view of a device 130 comprising a balloon 132 according to the present invention having members 134 and 136 located in a localized area on the perimeter of balloon 132. Members 134 and 136 may have the same or different (as shown) cross-sections.

In an alternate embodiment, FIGS. 5A, 5B, 5C and 5D illustrate the positioning of individual projections 104 and 106; 114; 124; and 134 and 136, respectively, on a balloon.

Figure 6A:
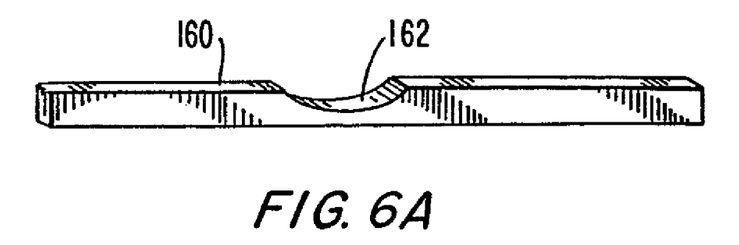
FIGS. 6A, 6B and 6C are diagrams showing stiffening members with areas of increased flexibility.
Figure 6B:
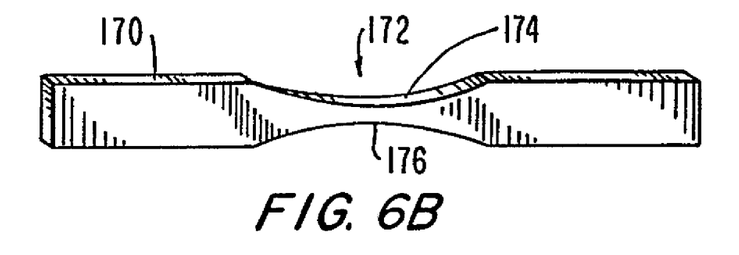
Figure 6C:
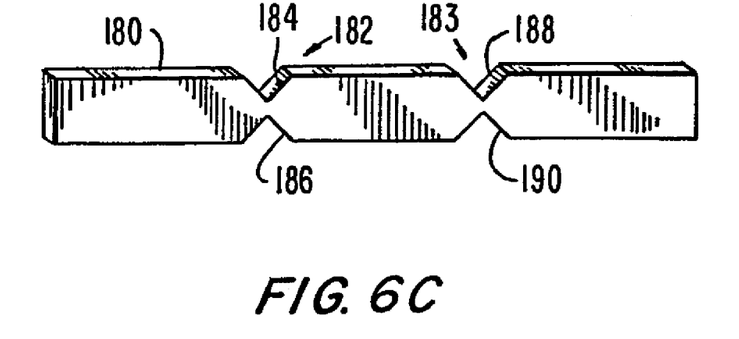

FIGS. 6A, 6B and 6C show alternative configurations for stiffening members according to the present invention. Each such configuration specifically creates a portion of the stiffening member where it may flex or pivot to facilitate navigation of the stiffening member through a curved passage. FIG. 6A shows a stiffening member 160 having a localized narrow area 162 which facilitates the flexing or pivoting of member 160 at an area 162. FIG. 6B shows a stiffening member 170 having a narrowed area 172 comprising cut-outs 174 and 176 which facilitate the flexing or pivoting of member 170 at an area 172. FIG. 6C shows a stiffening member 180 having narrowed areas 182 and 183 created by triangular cut outs 184 and 186, 188 and 190, respectively. Each of narrowed areas 182. and 183 is a point at which member 180 may flex or pivot.

Figure 7A:
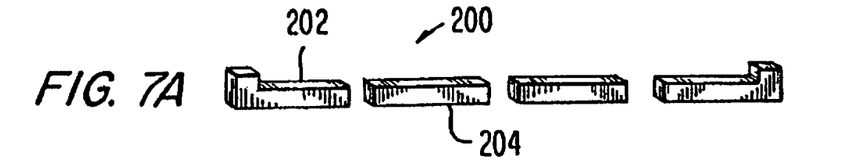
FIGS. 7A-7G are diagrams showing discontinuous stiffening members.
Figure 7B:
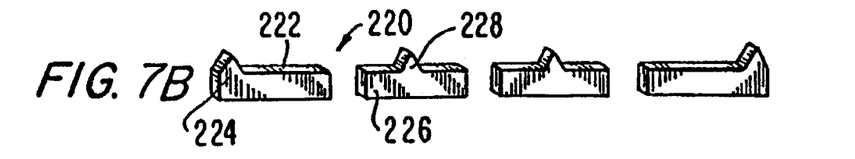
Figure 7C:
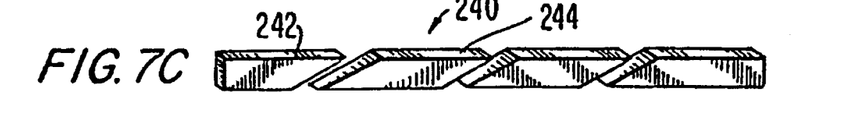
Figure 7D:
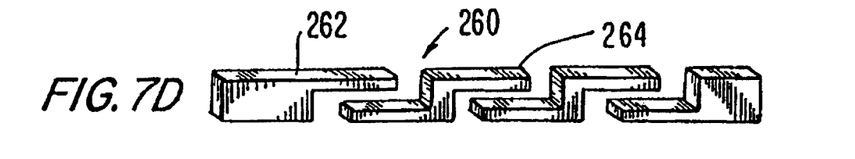
Figure 7E:
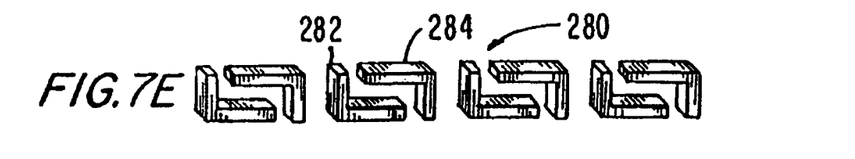
Figure 7F:
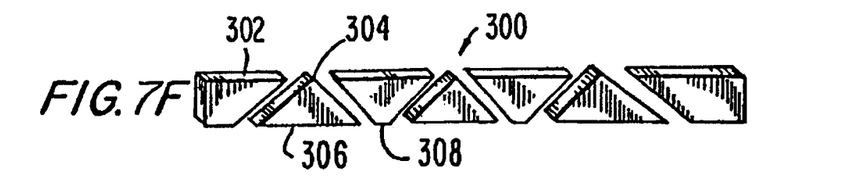

FIGS. 7A-7G show alternative designs for stiffening members according to the present invention. Each such alternative design provides discontinuous stiffening members that may be advantageously navigated through curved passages. FIG. 7A shows members 200 comprising end pieces 202 and interior pieces 204. Alternatively, one or more of pieces 202 and pieces 204 may be omitted. FIG. 7B shows members 220 comprising end pieces 222, having projections 224, and interior pieces 226 having projections 228. FIG. 7C shows members 240 comprising end pieces 242 and interior pieces 244. FIG. 7D shows members 260 comprising end pieces 262 and "S"-shaped interior pieces 264. FIG. 7E shows members 280 comprising "L"-shaped pieces 282 and 284. FIG. 7F shows members 300 comprising end pieces 302 and interior pieces 304. It should be noted that the surface area of interior pieces 304 along the surface of the balloon is greater than the surface area of pieces 308. As a consequence, upon expanding the balloon, pieces 306 will protrude above the upper surfaces of pieces 308.

Figure 7G:
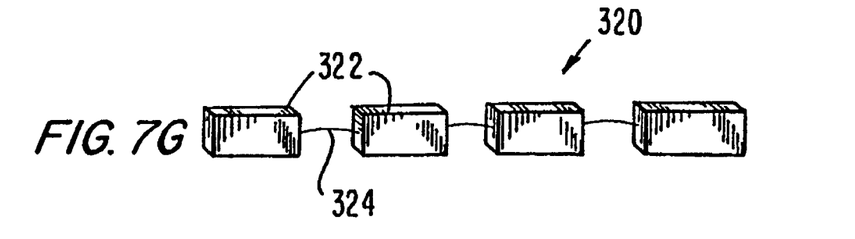

FIG. 7G shows members 320 comprising pieces 322 connected by filaments 324. Filaments 324 are preferably flexible but inelastic to limit the variation in positioning of members 320. Alternatively, filaments 324 are elastic.

Figure 8A:
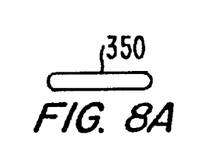
FIGS. 8A-8I are diagrams showing cross-sectional views of stiffening members.
Figure 8B:
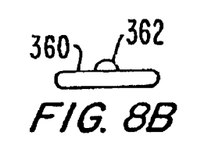
Figure 8C:
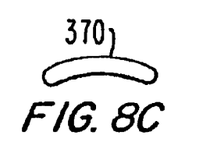
Figure 8D:
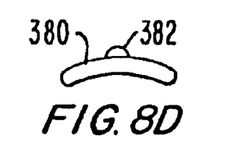
Figure 8E:
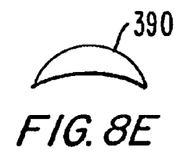
Figure 8F:
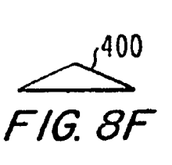
Figure 8G:
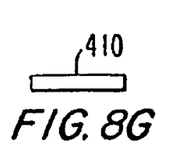
Figure 8H:
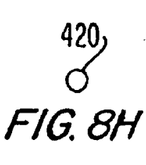
Figure 8I:
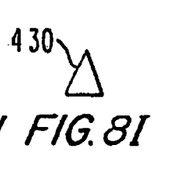

FIGS. 8A-I show cross-sectional views of numerous stiffening members according to the present invention. In FIG. 8A, a capsule-shaped cross-section 350 is shown. In FIG. 8B, a capsule-shaped cross-section 360 upon which a projection 362 is located is shown. In FIG. 8C, an arcuate cross-section 370 is shown. In FIG. 8D, an arcuate cross-section 380 with projection 382 is shown. In FIG. 8E, a crescent-shaped cross-section 390 is shown. In FIG. 8F, a triangular cross-section 400 is shown. In FIG. 8G, a rectilinear cross-section 410 is shown. Alternatively, it is contemplated that cross-section 410 may be modified by rounding its corners. In FIG. 8H, a circular cross-section 420 is shown. In FIG. 8I, an acute triangular cross-section 430 is shown.

Figures 9A, 9B:
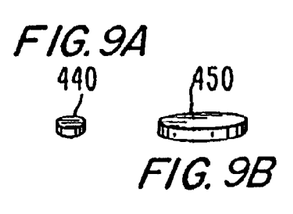
FIGS. 9A-9J are diagrams showing stiffening members.
Figures 9C, 9D, 9E:
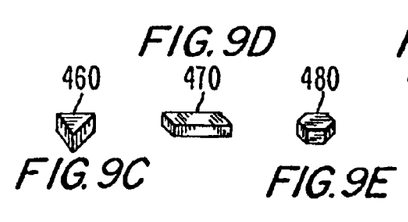
Figure 9F:
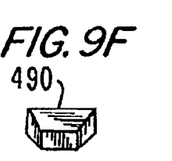
Figure 9G:
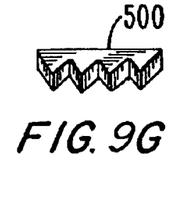
Figure 9H:
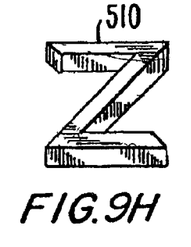
Figure 9I:
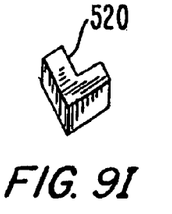
Figure 9J:
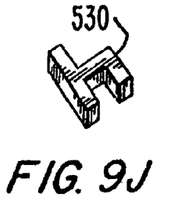

FIGS. 9A-J show perspective views of alternative embodiments of stiffening members according to the present invention. In FIG. 9A, a disc-shaped member 440 is shown. In FIG. 9B, an elliptical-shaped member 450 is shown. In FIG. 9C, a triangular-shaped member 460 is shown. In FIG. 9D, a rectilinear-shaped member 470 is shown. In FIG. 9E, a hexagonal-shaped member 480 is shown. In FIG. 9F, a trapezoidal-shaped member 490 is shown. In FIG. 9G, a sawtooth member 500 is shown. In FIG. 9H, a "Z"-shaped member 510 is shown. In FIG. 9I, an "L"-shaped member 520 is shown. In FIG. 9J a chair shaped member 530 is shown.

Figure 10A:
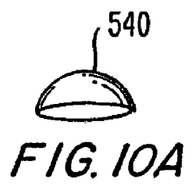
FIGS. 10A-10G are diagrams showing projections.
Figure 10B:
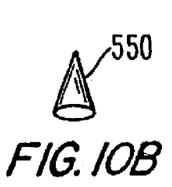
Figure 10C:
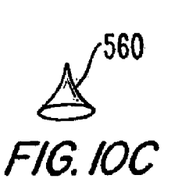
Figure 10D:
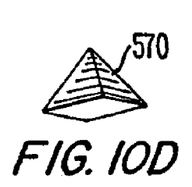
Figure 10E:
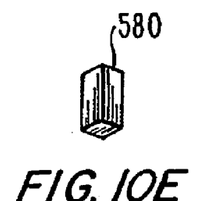
Figure 10F:
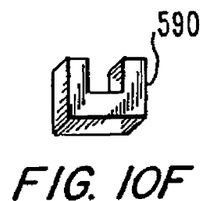
Figure 10G:
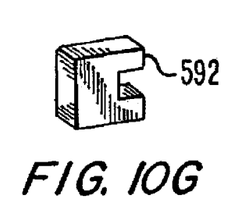

FIGS. 10A-G show alternate embodiments of projections according to the present invention. FIG. 10A shows a rounded projection 540. FIG. 10B shows a conical projection 550. FIG. 10C shows a pointed projection 560. FIG. 10D shows a pyramidal projection 570. FIG. 10E shows a post projection 580. FIG. 10F shows a "U"-shaped projection 590. FIG. 10G shows a "C"-shaped projection 592. Projection 540 is particularly adapted to crushing an occlusion. Projections 550, 560 and 570 are particularly adapted to engaging and piercing an occlusion and may be utilized to hold a stent or stent-graft. Projection 580 is the preferred embodiment of a projection for interdigitating or otherwise interfacing with a stent or stent-graft. Projection 590 provides a more complex structure for interdigitating with complementary structure on a stent or stent-graft and may be used to couple to a specific transversely oriented structural element of such a stent or stent-graft. Similarly, projection 592 may be utilized to hook or otherwise clamp a stent or stent-graft and may be particularly useful in exerting a pulling force. Projections 580, 590 and 592 may have blunt or pointed ends.

Figure 11:
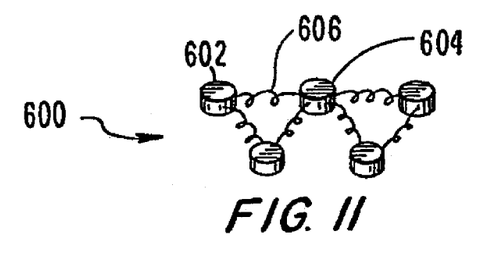
FIG. 11 is a diagram showing interconnected projections.

FIG. 11 illustrates a system 600 of interconnected projections. Projections 602 and 604 are connected by filaments 606. Filaments 606 may be comprised of an inelastic material or alternatively may be formed from an elastic material. Preferably, filaments 606 limit the variation in the positioning of the projections relative to each other. In this manner a network of projections may be interconnected to form a sheet, sheath or sleeve of projections that may be attached to a balloon.

Any of the stiffening members, projections or filaments described in the foregoing may be rendered opaque to x-rays or other radiation (collectively, "radio-opaque") to facilitate determination of the position of the balloon within a blood vessel and its position relative to the target lumen. In addition, radially arranged radio-opaque stiffeners or projections may be referenced to determine the degree of balloon expansion as a balloon is inflated. A single stiffening member that is radio-opaque along its length may be referenced to determine the axial and radial orientation of the balloon, including the amount of axial rotation. The stiffening members, projections and filaments may be made radio-opaque by conventional techniques, such as surface coating or printing, incorporation of radio-opaque material into the substance of the stiffening member (e.g., barium or bismuth salts blended into patterns) or construction of the stiffening member of a material with inherent radio-opacity, such as metallic tungsten.

A longitudinal stiffener with a longitudinally radio-opaque portion is advantageously utilized to reconfigure an expandable device that is already deployed within a lumen. Where such device has been deployed but requires reconfiguration, the position of the radio-opaque portion of the stiffener may be referenced to determine the location of the stiffener and guide its alignment with the expandable device. If a portion of the device requires further expansion, a small number of longitudinal stiffeners on a balloon may be aligned with the portion of the device requiring expansion to focus the radial force of expansion at the particular portion of the device. In this manner, a stiffened balloon with a longitudinal stiffener having a radio-opaque portion may be utilized to specifically further expand an end of a stent-graft that has not been properly deployed and has resulted in an endoleak.

For example, a balloon with a single radio-opaque longitudinal stiffener may be rotated to align the stiffener with an unexpanded portion of the stent-graft and expanded. Upon expansion of the balloon, the stiffener will exert a focussed force against the unexpanded portion of the stent-graft while the remainder of the balloon will exert less force at all other positions on its surface. Accordingly, the unexpanded portion of the stent-graft will be further expanded but the remainder of the stent-graft will not be expanded at all or will be expanded much less.

Similarly, utilizing a suitable configuration of projections, a stiffened balloon bearing a stiffening member having a projection may be utilized to push or pull a device expanded in a lumen to reposition it. Upon expansion of the balloon, the projection is oriented to fit a complementary interface at the device. The projection and the interface are connected and the device is repositioned by changing the position or orientation of the stiffened balloon.

While preferred embodiments of the invention have been described with particularity and with reference to the drawings, modifications and variations of the foregoing will be apparent to those of skill in the art utilizing the techniques disclosed herein. It is, therefore, to be understood that such embodiments are illustrative and not limiting on the scope of the present invention and that the invention encompasses such modifications and variations.

What is claimed is:

1. A stiffened balloon apparatus for use in passages in the human body that convey body fluids comprising:
    an expandable stiffened balloon having one or more longitudinally continuous stiffening members permanently attached to said balloon, said stiffening members being comprised of a material stiffer than the material of said balloon and being disposed along longitudinal perimeters of said balloon,
    wherein at least one of the stiffening members includes a pivot portion at which said stiffening member may flex or pivot to facilitate navigation of the stiffened balloon through a curved passage, said pivot portion having a localized narrowed area of said stiffening member and being characterized by a relative absence of stiffener material in a radially outward-most part of said stiffening member extending from one lateral side of said stiffening member to the other lateral side of said stiffening member, and a smaller cross-sectional area relative to the cross-sectional areas of the stiffening member adjacent to said localized narrowed area,
    wherein said pivot portion comprises a cut-out constituting a minor fraction of the length of said stiffening member at which the stiffening member flexes or pivots.

2. The apparatus of claim 1 wherein one or more stiffening members comprise a cutting element.

3. A stiffened balloon apparatus for use in passages in the human body that convey bodily fluids comprising:
    an expandable stiffened balloon having one or more elongate, longitudinally continuous stiffening members permanently attached to said balloon, said stiffening members being comprised of a material stiffer than the material of said balloon and being disposed along longitudinal perimeters of said balloon,
    wherein at least one of the said stiffening members includes a pivot portion at which said stiffening member may flex or pivot to facilitate navigation of said balloon through a curved passage, said pivot portion comprising a localized narrowed area of said stiffening member constituting a minor fraction of the length of said stiffening member at which the stiffening member flexes or pivots and being characterized by a cut-out in a lateral side of said stiffening member and a smaller cross-sectional area relative to the cross-sectional areas of the stiffening member adjacent to said localized narrowed area.

4. The apparatus of claim 3 wherein said cut-out extends from the radially inward-most part of said stiffening member to the radially outward-most part thereof.

5. The apparatus of claim 4 wherein said cut-out constitutes a minor fraction of the length of said stiffening member at which the stiffening member flexes or pivots.

6. The apparatus of claim 3 wherein one or more of said stiffening members comprise a region that is radio-opaque.

7. The apparatus of claim 6 wherein a longitudinal portion of one or more stiffening members comprises a material that is substantially more radio-opaque than the constituent material of another longitudinal portion of said stiffening member.

8. The apparatus of claim 3 wherein one or more stiffening members comprise a cutting element.

9. The apparatus of claim 3 further characterized by a relative absence of stiffener material in a radially inward-most part of said stiffening member.

10. The apparatus of claim 8 wherein the absences of stiffener material in the radially outward-most and inward-most parts are longitudinally nonaligned with one another.

11. The apparatus of claim 3 wherein said cut-out has a geometric shape.

12. The apparatus of claim 3 wherein one or more stiffening members include at least one projection.

13. A stiffened balloon apparatus for use in passages in the human body that convey bodily fluids comprising:
    an expandable stiffened balloon having one or more elongate, longitudinally continuous stiffening members permanently attached to said balloon, said stiffening members being comprised of a material stiffer than the material of said balloon and being disposed along longitudinal perimeters of said balloon,
    wherein at least one of said stiffening members includes a pivot portion at which said stiffening member may flex or pivot to facilitate navigation of said balloon through a curved passage, said pivot portion comprising a localized narrowed area of said stiffening member and being characterized by a relative absence of stiffener material extending from a radially inward-most to a radially outward-most part thereof across the entire dimension of the lateral side of said stiffening member and a smaller cross-sectional area relative to the cross-sectional areas of the stiffening member adjacent to said localized narrowed area.

14. A stiffened balloon apparatus for use in passages in the human body that convey bodily fluids comprising:
an expandable stiffened balloon having one or more elongate, longitudinally continuous stiffening members permanently attached to said balloon, said stiffening members being comprised of a material stiffer than the material of said balloon and being disposed along longitudinal perimeters of said balloon,
wherein at least one of the said stiffening members includes a pivot portion at which said stiffening member may flex or pivot to facilitate navigation of said balloon through a curved passage, said pivot portion comprising a localized narrowed area of said stiffening member constituting a minor fraction of the length of said stiffening member at which the stiffening member flexes or pivots and being characterized by a relative absence of stiffener material in a lateral side thereof and a smaller cross-sectional area relative to the cross-sectional areas of the stiffening member adjacent to said localized narrowed area.

15. The apparatus of claim 14 further comprising an additional pivot portion, said additional pivot portion characterized by a relative absence of stiffener material in the radially inward-most part of said stiffening member extending from one lateral side of said stiffening member to the other lateral side of said stiffening member.

16. The apparatus of claim 14 wherein said pivot portion comprises a cut-out extending from a radially inward-most to a radially outward-most part thereof across the entire dimension of said lateral side of said stiffening member.

17. The apparatus of claim 14 wherein one or more stiffening members include a plurality of pivot portions.

18. The apparatus of claim 14 wherein at least a portion of one or more stiffening members has a cross-section with a perimeter that includes a curvilinear portion.

19. The apparatus of claim 14 wherein at least a portion of one or more stiffening members has a polygonal cross-section.

20. The apparatus of claim 14 wherein one or more stiffening members, in cross-section, have a radially inward-most surface that is wider than a radially outward-most surface.

21. The apparatus of claim 14 wherein one or more stiffening members, in cross-section, have a curvilinear taper from its bottom portion in contact with the balloon surface to its apex at the top portion.

22. The apparatus of claim 14 wherein one or more stiffening members are no longer than three-quarters of the length of said balloon.

23. The apparatus of claim 22 wherein an end of one or more stiffening members is disposed at an end of said balloon.

24. The apparatus of claim 14 wherein one or more stiffening members are located partly or entirely within a wall of said balloon.

25. The apparatus of claim 14 wherein one or more stiffening members are disposed on a sheet of material adapted to be applied to said balloon.

26. The apparatus of claim 14 wherein one or more stiffening members are comprised of metal, plastic, composite or fiber material.

27. The apparatus of claim 14 having a plurality of stiffening members.

28. The apparatus of claim 14 wherein at least one of the stiffening members is directly connected to another of said stiffening members.

29. The apparatus of claim 14 wherein one or more of said stiffening members comprises a region that is radio-opaque.

30. The apparatus of claim 29 wherein a longitudinal portion of one or more stiffening members comprises a material that is substantially more radio-opaque than the constituent material of another longitudinal portion of said stiffening member.

31. The apparatus of claim 30 wherein said projection is pointed.

32. The apparatus of claim 30 wherein said projection is sufficiently sharp to pierce an occlusive material.

33. The apparatus of claim 29 wherein said radio-opaque region is comprised of metallic tungsten or a barium or bismuth salt.

34. The apparatus of claim 14 wherein one or more stiffening members include at least one projection.

35. The apparatus of claim 14 wherein one or more stiffening members comprise means for engaging an occlusive material in a lumen.

36. The apparatus of claim 14 wherein said pivot portion comprises a notch or cut-out in said lateral side.

37. The apparatus of claim 36 wherein said notch or cut-out has a curvilinear portion.

38. The apparatus of claim 36 wherein said notch or cut-out has a geometric shape.

39. The apparatus of claim 14 wherein said pivot portion is located within the central one third of the length of the at least one stiffening members.

40. The apparatus of claim 14 wherein one or more stiffening members comprise a cutting element.

41. The apparatus of claim 14 further characterized by a relative absence of stiffener material in a radially inward-most part of said stiffening member.

42. The apparatus of claim 41 wherein the absences of stiffener material in the radially outward-most and inward-most parts are longitudinally nonaligned with one another.

43. apparatus for use in passages in the human body that convey bodily fluids comprising:
an expandable stiffened balloon having two or more elongate, longitudinally continuous stiffening members permanently attached to said balloon, said stiffening members being comprised of a material stiffer than the material of said balloon and being disposed along longitudinal perimeters of said balloon,
wherein at least one of said stiffening members includes a first pivot portion at which said stiffening member may flex or pivot to facilitate navigation of the stiffened balloon through a curved passage, said first pivot portion comprising a first localized narrowed area of the stiffening member constituting a first minor fraction of the length of the stiffening member at which the stiffening member flexes or pivots and being characterized by a relative absence of stiffener material in a first radially outward-most part of the stiffening member and a first smaller cross-sectional area relative to the cross-sectional areas of the stiffening member adjacent to said first localized narrowed area; and
wherein at least a second of said stiffening members includes a second pivot portion at which said second stiffening member may flex or pivot to facilitate navigation of the stiffened balloon through said curved passage, said second pivot portion comprising a second localized narrowed area of said second stiffening member constituting a second minor fraction of the length of the second stiffening member at which said second stiffening member flexes or pivots and being characterized by a cut-out extending from a radially inward-most part of said second stiffening member to a radially outward-most part thereof across at least a portion of the lateral side of said second stiffening member and a second smaller cross-sectional area relative to the cross-sectional areas of the second stiffening member adjacent to said second localized narrowed area.

44. The apparatus of claim 43 wherein said one of said stiffening members and/or said second of said stiffening members further comprises an additional pivot portion, said additional pivot portion comprising a localized narrowed area of said stiffening member characterized by a relative absence of stiffener material in a radially inward-most part thereof and a smaller cross-sectional area relative to the cross-sectional areas of the stiffening member adjacent to said localized narrowed area.

45. apparatus for use in passages in the human body that convey body fluids comprising:
an expandable stiffened balloon having one or more elongate, longitudinally continuous stiffening members permanently attached to said balloon, said stiffening members being comprised of a material stiffer than the material of said balloon and being disposed along longitudinal perimeters of said balloon,
wherein at least one of said stiffening members includes a pivot portion at which said stiffening member may flex or pivot to facilitate navigation of the stiffened balloon through a curved passage, said pivot portion comprising a localized narrowed area of said stiffening member constituting a minor fraction of the length of said stiffening member at which the stiffening member flexes or pivots and being characterized by a relative absence of stiffener material in a radially outward-most part thereof and in a lateral side thereof, and a smaller cross-sectional area relative to the cross-sectional areas of the stiffening member adjacent to said localized narrowed area.

46. The apparatus of claim 45 wherein one or more stiffening members include a plurality of pivot portions.

47. The apparatus of claim 45 therein each lateral side of said stiffening member includes a notch or cut-out, and said notches or cut-outs are longitudinally aligned with one another.

48. apparatus for use in passages in the human body that convey body fluids comprising:
an expandable stiffened balloon having one or more elongate, longitudinally continuous stiffening members permanently attached to said balloon, said stiffening members being comprised of a material stiffer than the material of said balloon and being disposed along longitudinal perimeters of said balloon,
wherein at least one of the stiffening members includes at least one pivot portion at which said stiffening member may flex or pivot to facilitate navigation of the stiffened balloon through a curved passage, said pivot portion comprising a localized narrowed area of said stiffening member constituting a minor fraction of the length of said stiffening member at which the stiffening member flexes or pivots and being characterized by a relative absence of stiffener material in a radially outward-most part thereof and in a radially inward-most part thereof and in a lateral side thereof, said absence of material in said radially inward-most part extending from one lateral side of said stiffening member to the other lateral side of said stiffening member, and a smaller cross-sectional area relative to the cross-sectional areas of the stiffening member adjacent portions of to said member localized narrowed area.

49. The apparatus of claim 48 wherein the absences of stiffener material in the radially outward-most part and radially inward-most part and in a lateral side are each longitudinally nonaligned with one another.

* * * * *